US009573154B2

(12) United States Patent
Bretillot et al.

(10) Patent No.: US 9,573,154 B2
(45) Date of Patent: Feb. 21, 2017

(54) DISPENSING AEROSOLS

(71) Applicant: AERODESIGNS, INC., Cambridge, MA (US)

(72) Inventors: Marc Bretillot, Paris (FR); David A. Edwards, Boston, MA (US)

(*) Notice: Subject to any disclaimer, the term of this patent is extended or adjusted under 35 U.S.C. 154(b) by 207 days.

(21) Appl. No.: 14/353,346

(22) PCT Filed: Oct. 24, 2012

(86) PCT No.: PCT/US2012/061695
§ 371 (c)(1),
(2) Date: Apr. 22, 2014

(87) PCT Pub. No.: WO2013/063119
PCT Pub. Date: May 2, 2013

(65) Prior Publication Data
US 2014/0291414 A1 Oct. 2, 2014

Related U.S. Application Data

(60) Provisional application No. 61/550,869, filed on Oct. 24, 2011.

(51) Int. Cl.
*A61L 9/03* (2006.01)
*B05B 17/06* (2006.01)
(Continued)

(52) U.S. Cl.
CPC ...... *B05B 17/0615* (2013.01); *A61M 15/0025* (2014.02); *A61M 15/0085* (2013.01);
(Continued)

(58) Field of Classification Search
CPC .............. B05B 12/081; B05B 17/06–17/0669; A61M 15/0085; A61M 15/0025; A61M 2205/3386; A61M 2205/8206; A61M 2209/084; A61M 2209/08; A61L 2209/132; A61L 9/03–9/037
(Continued)

(56) References Cited

U.S. PATENT DOCUMENTS 2,844,469 A 7/1958 Melnick et al.
3,163,544 A 12/1964 Valyi
(Continued)

FOREIGN PATENT DOCUMENTS

GB 2469876 11/2010
JP 05-277188 A 10/1993
(Continued)

OTHER PUBLICATIONS

International Search Report from corresponding PCT Application No. PCT/US2012/061695 dated May 22, 2013.

*Primary Examiner* — Arthur O Hall
*Assistant Examiner* — Juan C Barrera
(74) *Attorney, Agent, or Firm* — Seed IP Law Group LLP

(57) ABSTRACT

A device (200) for generating an aerosol cloud, the device (200) comprising: a body (210) defining an inner cavity, an outer surface, and an opening (213) extending between the inner cavity of the body (210) and the outer surface; at least one ultrasonic element (220) operable to aerosolize a liquid disposed in the inner cavity; and at least one sensor (226) associated with the at least one ultrasonic element (220).

11 Claims, 10 Drawing Sheets

(51) Int. Cl.
*A61M 15/00* (2006.01)
*B05B 12/08* (2006.01)

(52) U.S. Cl.
CPC ............... *B05B 12/081* (2013.01); *A61L 9/03* (2013.01); *A61M 2205/3386* (2013.01); *A61M 2205/8206* (2013.01); *A61M 2209/084* (2013.01)

(58) Field of Classification Search
USPC .................. 239/68, 34–60, 102.1, 102.2
See application file for complete search history.

(56) References Cited

U.S. PATENT DOCUMENTS

| | | | |
|---|---|---|---|
| 4,790,479 A | 12/1988 | Matsumoto et al. | |
| 5,170,782 A | 12/1992 | Kocinski | |
| 5,908,158 A | 6/1999 | Cheiman | |
| 6,152,383 A | 11/2000 | Chen | |
| 7,201,167 B2 | 4/2007 | Fink et al. | |
| 7,963,460 B2* | 6/2011 | Jorgensen | A61L 9/122 239/102.1 |
| 8,336,545 B2 | 12/2012 | Fink et al. | |
| 2006/0137680 A1 | 6/2006 | Sheiman | |
| 2008/0245362 A1 | 10/2008 | Moessis et al. | |
| 2008/0299049 A1* | 12/2008 | Stangl | A61M 15/0085 424/45 |
| 2011/0024521 A1* | 2/2011 | Jorgensen | B05B 17/0615 239/102.1 |
| 2011/0049266 A1* | 3/2011 | Jorgensen | A61L 9/03 239/338 |
| 2011/0079660 A1* | 4/2011 | Jorgensen | A61L 9/14 239/144 |
| 2011/0280767 A1* | 11/2011 | Goessens | A61L 9/14 422/106 |

FOREIGN PATENT DOCUMENTS

| | | |
|---|---|---|
| JP | 11-504567 A | 4/1999 |
| JP | 2005-538822 A | 12/2005 |
| WO | 97/31721 A1 | 9/1997 |
| WO | 2004/017848 A1 | 3/2004 |
| WO | 2007/117675 A2 | 10/2007 |
| WO | 2010/065744 A2 | 6/2010 |

* cited by examiner

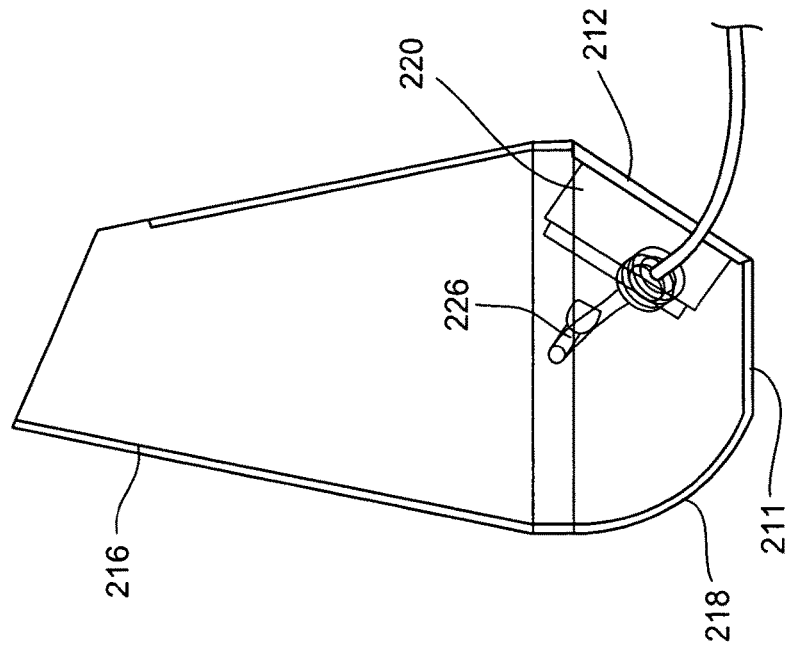
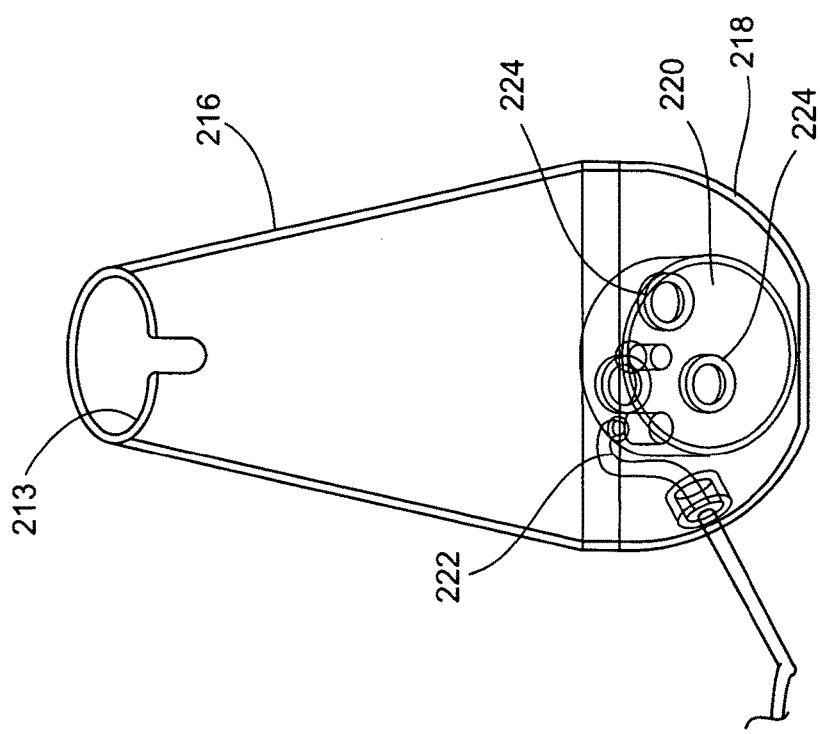
FIG. 2F
FIG. 2E

DISPENSING AEROSOLS

RELATED APPLICATIONS

This application is the U.S. National Stage of International Application No. PCT/US2012/061695, filed Oct. 24, 2012, published in English, which claims the benefit of U.S. Provisional Application No. 61/550,869, filed on Oct. 24, 2011, the entire teachings of these applications are incorporated herein by reference.

TECHNICAL FIELD

This invention relates to dispensing aerosols.

BACKGROUND

Aerosol particles can be used to deliver substances to various parts of the body. These particles have been used, for example, for drug delivery.

SUMMARY

The devices and methods for dispensing aerosols described below include both devices and methods for generating aerosols, and devices and methods for consuming the aerosols. These devices and methods, for example, can be used to generate aerosol clouds from liquids for consumption by users. The aerosol clouds can be used for nutrient delivery, taste delivery, and in weight-loss programs. Designed for ease of use, these devices and methods can be incorporated into settings including, for example, home kitchens, restaurants, and bars.

Aerosol clouds can be generated from beverages such as cocktails and juices. For example, liquids or essences dispensed can include coffees and teas, vitamin-reinforced water, and energy-enhancing substances. Aerosol clouds can be generated and used to dispense liquids and essences such as liquid pastries and liquid foods to provide an exceptional taste experience with few calories. These devices and methods can also be used for delivery of substances including medicines, dietary supplements, botanicals, caffeine, vitamins, and appetite-control herbs.

Food delivery apparatuses can produce aerosol clouds of edible substances by ultrasonication of liquids. These clouds can be inhaled for ingestion, avoiding the respiratory tract, when particle sizes are sufficiently large and the cloud is "inhaled" (for example, carried via air that is breathed into the respiratory tract, or via air that is sucked into the mouth.)

Please note that throughout, references to "inhalation", "ingestion", and other related terms are not necessarily intended to be understood within the context of official definitions for foods, dietary supplements, and/or drugs. Rather, they are intended, in general, to refer to one or more acts that involve the movement of air in the mouth (e.g., breathing in air that then travels to the lungs; sucking in air that remains in the mouth; etc.) and/or that involve the transfer of a consumable substance to the body (e.g. vitamins depositing somewhere within the mouth; dietary supplements depositing on particular surfaces of the mouth; etc.). In some cases, such terms as "inhalable" and "breathable" may be used interchangeably, and in some cases, such terms as "ingestible", "consumable", and "edible" may be used interchangeably. Ingestible aerosol clouds can be produced through ultrasonication and/or other means, and delivered in such ways as to avoid potential problems, and present many advantages, as an inhaled eating experience. In some embodiments, food delivery devices (e.g., aerosol generation and/or dispensing and/or delivery devices) displace the aerosol cloud laterally relative to the source of the aerosol cloud, such that large particles rise and fall over the source, while smaller particles—particularly if lateral movement of the cloud can occur very near to the surface of the liquid—move by diffusion and convection laterally, escaping the falling large droplets.

Large and intermediate droplets that convect laterally fall by gravity, so if a lateral chamber is provided that can contain an aerosol cloud, a cloud of fine aerosol particles can be made to be a stable standing cloud. This cloud can be designed to be of a certain size, have a certain aerosol density, and/or possess particles in a desired mouth-delivery or other range, by, for example, manipulation of the dimensions of the cloud container, manipulation of the properties of the liquid (e.g, surface tension, or size of dissolved particles), manipulation of the properties of the aerosol generator (e.g, the frequency of piezo-electric vibrations), or manipulation of environmental conditions (e.g., liquid/air temperature or humidity). Notably, surface tensions lower than ~72 dynes/cm can be achieved with the use of surfactants, which may produce excellent standing cloud aerosols. Further, an aperture or faucet can be provided whereby the cloud may be poured into glasses or other receptacles, or whereby a further delivery device may be inserted—a convenient and useful way of eating substances by an intake of air by the user.

In some aspects, devices for generating an aerosol cloud include: a body defining an inner cavity; at least one piezoelectric element operable to aerosolize a liquid disposed in the inner cavity defined by the body; a sensor connected to the at least one piezoelectric element such that the sensor activates the at least one piezoelectric element in the presence of liquid. Embodiments can include one or more of the following features.

In some embodiments, the sensor deactivates the at least one piezoelectric element in the absence of liquid.

In some embodiments, the body defines an opening extending between the inner cavity of the body and an outer surface of the body. In some cases, the at least one piezoelectric element is operable to emit energy substantially along an axis that is offset from the opening extending between the inner cavity of the body and the outer surface of the body. In some cases, the body has a first stable equilibrium position and a second equilibrium position such that the opening is higher when the body is in the first stable equilibrium position than when the body is in the second equilibrium position and such that the at least one piezoelectric element is operable to emit energy substantially vertically when the body is in the second equilibrium position.

In some embodiments, the device also includes a side port configured to engage a fluid cartridge. In some cases, the device is configured such that suction forces and/or gravity effects can be used to transfer fluid from the fluid cartridge to the inner cavity of the body of the device. In some cases, the devices include a pump operable to transfer fluid from the fluid cartridge to the inner cavity of the body of the device.

In some aspects, devices include: a primary member with a size selected to cover a container, particularly wherein the primary member comprises one or more of the following materials: glass, plastic, ceramic, metal, fabric, paper; and a tubular member used in connection with the primary member, the tubular member providing fluid communication between a first side of the primary member and an second side of the primary member opposite the first side. Embodiments can include one or more of the following features.

In some embodiment's, the tubular member comprises one or more of the following materials: glass, plastic, ceramic, metal.

In some embodiments, the tubular member extends from the first side of the primary member. In some cases, the tubular member extends from the second side of the primary member.

In some embodiments, devices also include a container with an opening configured to be sealed by the primary member to an extent that impacts air convection inside the container.

In some embodiments, the primary member is disc-shaped.

In some aspects, devices include a tubular member extending from an open first end to a closed second end opposite the first end, a mouthpiece at the second end having apertures extending through sides of the tubular member.

In some aspects, systems include: a container with an inner cavity having a volume of between about 6 ounces and 20 ounces; and at least one piezoelectric element operable to aerosolize a liquid disposed in the inner cavity defined by the body. Embodiments can include one or more of the following features.

In some embodiments, systems also include a stand configured to receive and engage the container. In some cases, the at least one piezoelectric element is disposed in the container. In some cases, systems include a switch controlling operation of the at least one piezoelectric element. In some cases, the at least one piezoelectric element is disposed in the stand. In some cases, the systems also include contacts that can activate at least one piezoelectric element when the stand receives and engages the container.

In some aspects, devices include a fluid cartridge containing a concentrated form of a liquid, wherein the concentrated form of a liquid is rendered more appropriate for consumption by being aerosolized. In some cases, the device is configured to aerosolize the liquid and substantially deliver the aerosol to the sides of a mouth of a user.

In some aspects, devices for generating an aerosol cloud include: a body defining an inner cavity, an outer surface, and an opening extending between the inner cavity of the body and the outer surface; at least one ultrasonic element operable to aerosolize a liquid disposed in the inner cavity; and at least one sensor associated with the at least one ultrasonic element.

Embodiments can include one or more of the following features. The at least one ultrasonic element comprises a piezoelectric element. The at least one sensor is a fluid sensor. The at least one ultrasonic element is disposed within the body defining the inner cavity. The at least one ultrasonic element is operable to emit energy substantially along an axis that is offset from the opening extending between the inner cavity of the body and the outer surface of the body. The sensor activity is determined by an orientation of the body. The body has a first stable equilibrium position and a second equilibrium position such that the opening is higher when the body is in the first stable equilibrium position than when the body is in the second equilibrium position and such that the at least one ultrasonic element is operable to emit energy substantially vertically when the body is in the second equilibrium position. The at least one sensor activates the at least one ultrasonic element in the presence of liquid or deactivates the at least one ultrasonic element in the absence of liquid. The device includes a detachable stand configured to receive and engage the body. The at least one ultrasonic element is disposed in the stand. The at least one sensor comprises a contact operable to activate at least one ultrasonic element when the stand receives and engages the body. The device includes a port configured to engage a fluid cartridge. The device is configured such that suction forces and/or gravity effects transfer fluid from the fluid cartridge to the inner cavity. The device includes a pump operable to transfer fluid from the fluid cartridge to the inner cavity. The device includes a switch controlling operation of the at least one sensor and/or the at least one ultrasonic element. The device includes at least one tubular member providing fluid communication out of the interior cavity. The tubular member comprises an open first end, and a closed second end opposite the first end, the second end having apertures extending through sides of the tubular member. The open first end of the tubular member comprises a component which engages a straw received within the open first end. The device includes a primary member with a size selected to enclose the opening of the body. The device includes at least one tubular member extending from a first side of the primary member. The device includes at least one tubular member extending from a second side of the primary member. The primary member further comprises at least one aperture configured to receive at least one tubular member. The device includes at least one tubular member extending from the interior cavity, through the aperture of the primary member, to a second side of the primary member opposite the first side.

In some aspects, a system includes a container with an inner cavity having a volume of between about 6 ounces and 20 ounces; and at least one ultrasonic element operable to aerosolize a liquid disposed in the inner cavity defined by the body.

Embodiments can include one or more of the following features. The at least one ultrasonic element is operable to emit energy substantially along an axis that is offset from the opening extending between the inner cavity of the body and the outer surface of the body. The body has a first stable equilibrium position and a second equilibrium position such that the opening is higher when the body is in the first stable equilibrium position than when the body is in the second equilibrium position and such that the at least one ultrasonic element is operable to emit energy substantially vertically when the body is in the second equilibrium position. The system includes a detachable stand configured to receive and engage the body. The at to least one ultrasonic element is disposed in the stand. The system includes a port configured to engage a fluid cartridge. The system is configured such that suction forces and/or gravity effects transfer fluid from the fluid cartridge to the inner cavity. The system includes a pump operable to transfer fluid from the fluid cartridge to the inner cavity. The system includes at least one tubular member providing fluid communication out of the interior cavity. The tubular member comprises an open first end, and a closed second end opposite the first end, the second end having apertures extending through sides of the tubular member. The open first end of the tubular member comprises a component which engages a straw received within the open first end. The system includes a primary member with a size selected to enclose the opening of the body. The system includes at least one tubular member extending from a first side of the primary member. The system includes at least one tubular member extending from a second side of the primary member. The primary member further includes at least one aperture configured to receive at least one tubular member. The system includes at least one tubular member extending from the interior cavity, through the aperture of the primary member, to a second side of the primary member opposite the first side.

In some aspects, a device includes a tubular member, wherein the tubular member comprises an open first end, and a closed second end opposite the first end, the open first end designed to receive a straw and a mouthpiece at the second end having apertures extending through the sides of the tubular member.

These devices and methods can be designed for very concentrated systems, where the goal is to deliver meaningful amounts of nutrients, vitamins, dietary supplements, etc. by concentrating a substance (e.g. coffee, tea, botanicals, or other substances with the desired nutrients, vitamins, etc.), in such a way that you would want to prevent someone from drinking an initial fluid form, but in which it would be appropriate or desirable for the person to sip an ensuing cloud form. In some aspects, these devices and methods include a cartridge designed to deliver highly concentrated liquids to the dispensing device, to be aerosolized in such a way as to avoid direct human contact with the liquid, but enable consumption of the generated aerosol cloud.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2E-2H are various views of a prototype of the aerosol dispensing device of FIGS. 2A-2D.

Like reference symbols in the various drawings indicate like elements.

DETAILED DESCRIPTION

Figures 1A, 1B:
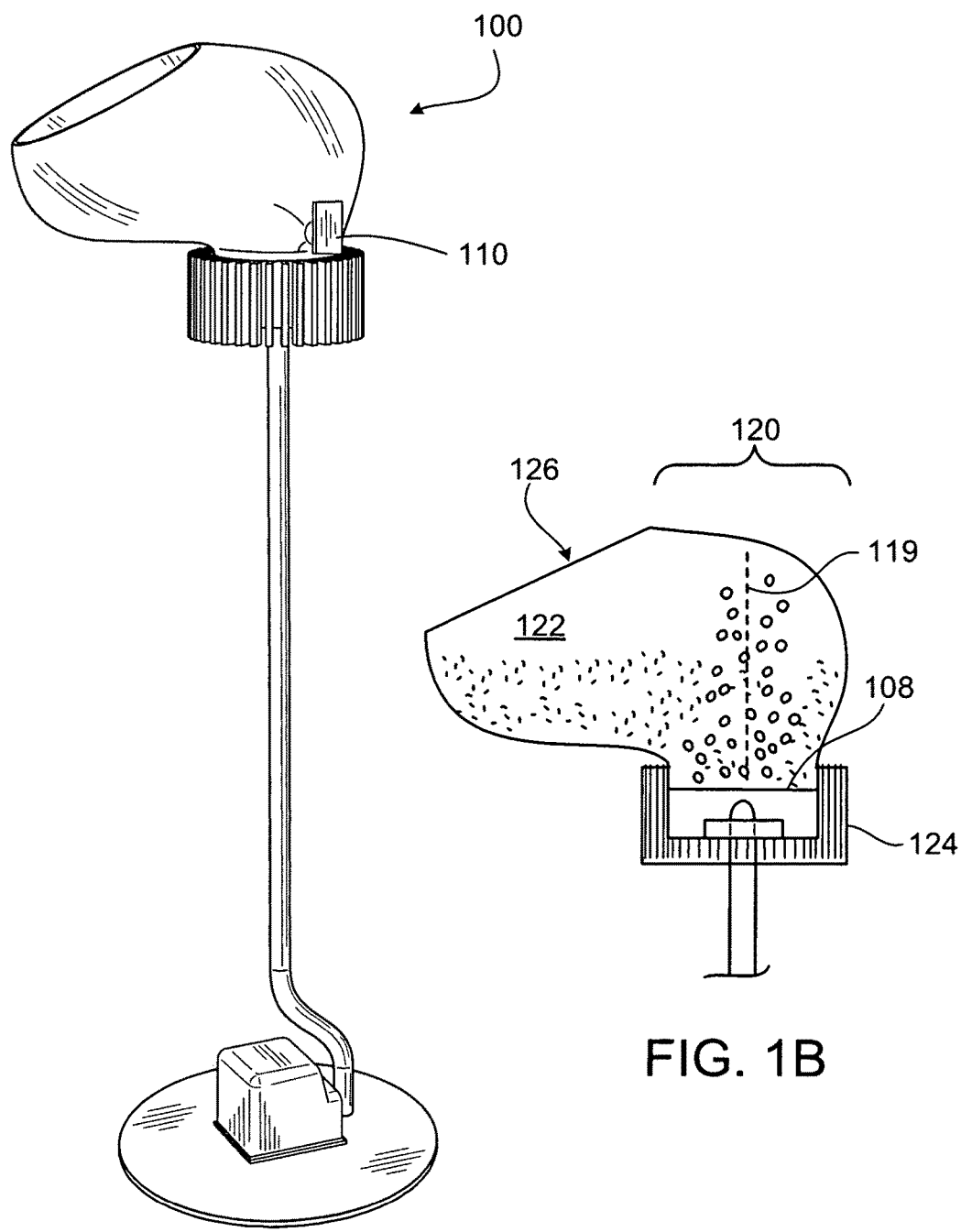
FIGS. 1A and 1B are, respectively, a perspective view and a cross-sectional view of an aerosol dispensing device.
Figure 2A:
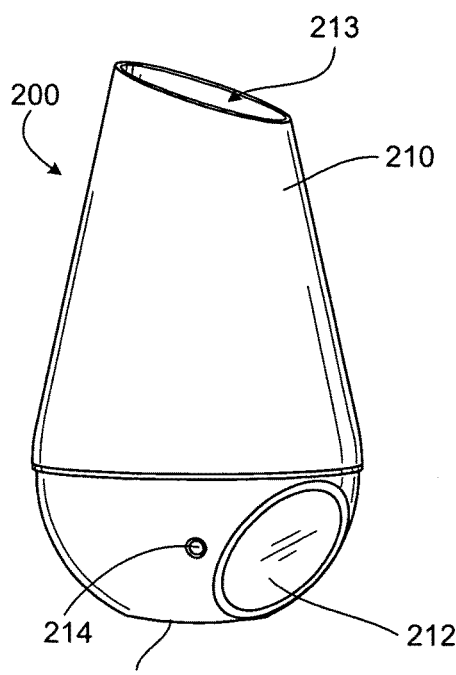
FIGS. 2A-2D are perspective views of an aerosol dispensing device.
Figure 2B:
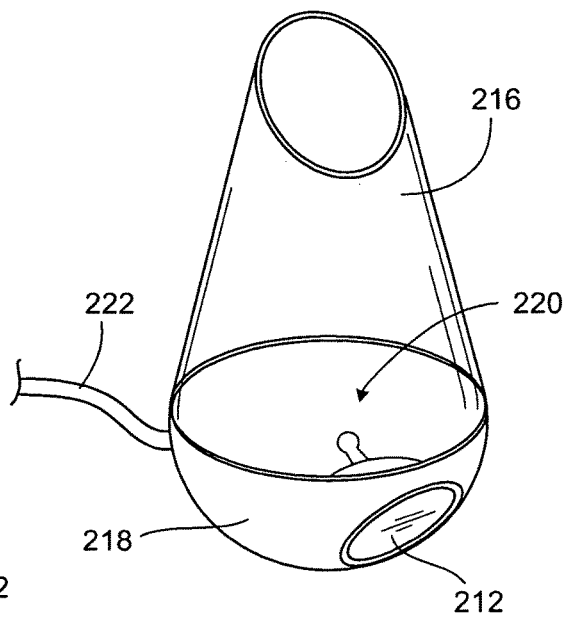
Figure 2C:
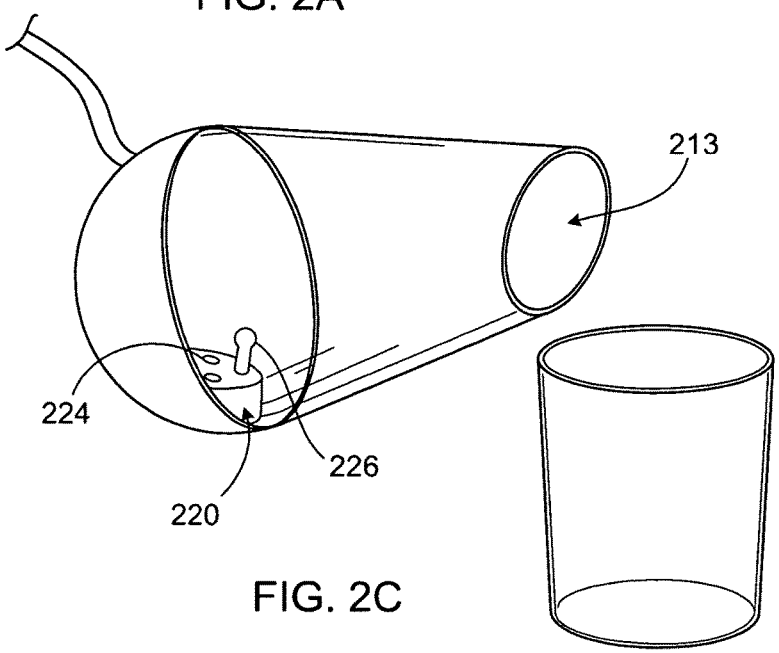
Figure 2D:
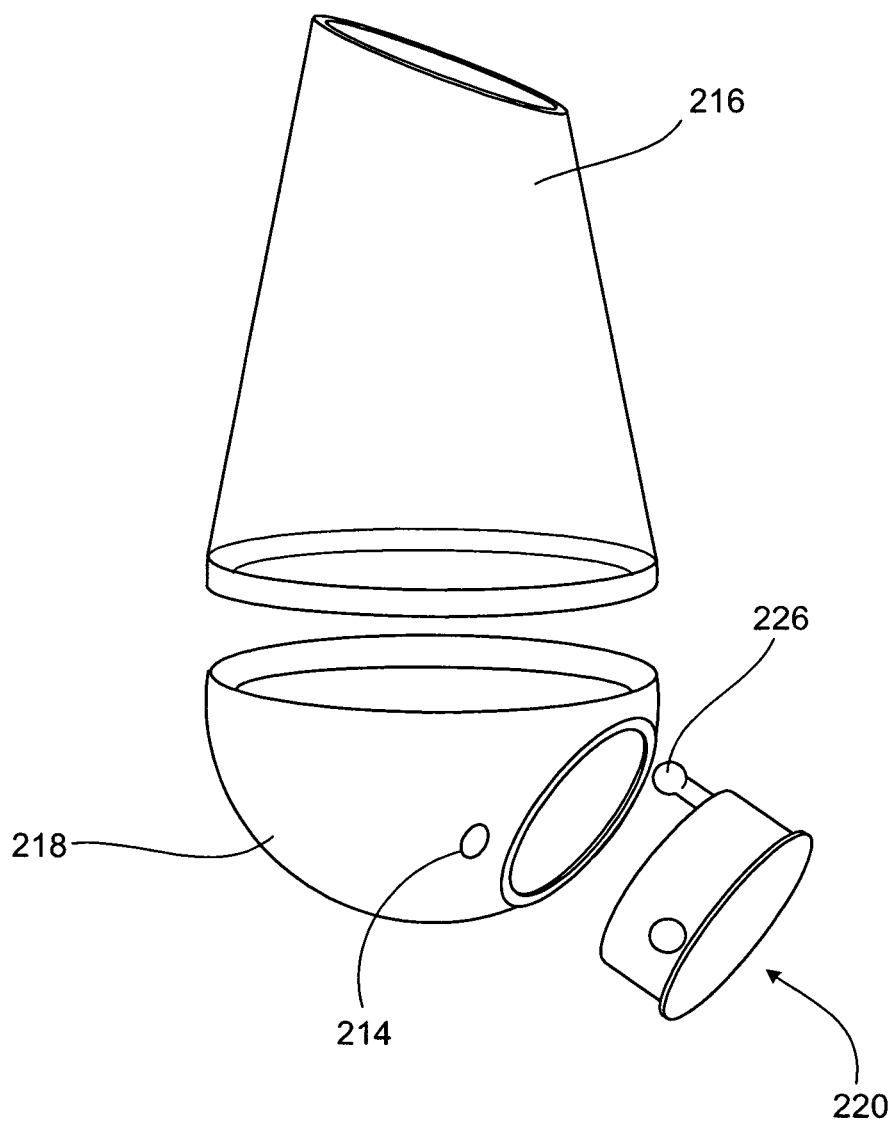
Figure 2H:
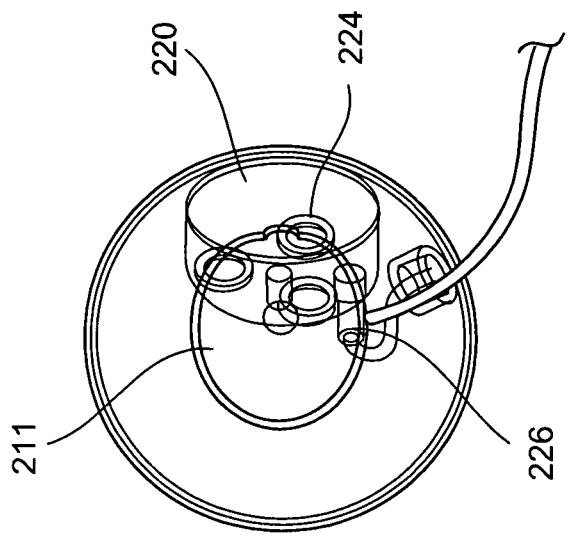
Figure 2G:
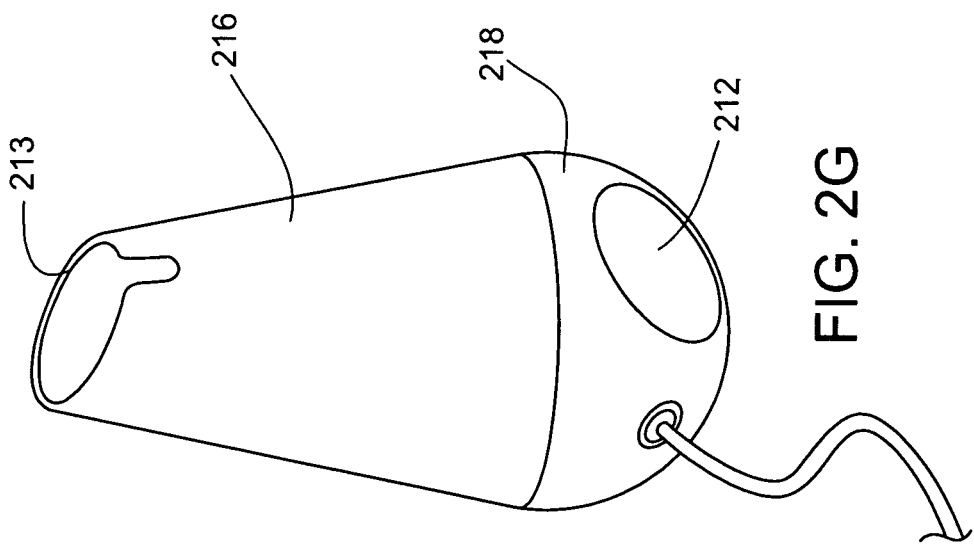

An aerosol delivery device 100 as depicted in FIGS. 1A and 1B was designed to generate and deliver aerosols clouds such as, for example, aerosolized beverages. The aerosol clouds are generated from a liquid placed in the delivery device 100.

Aerosol clouds of edible substances can be made by ultrasonication of liquids. These clouds can be "inhaled for ingestion", avoiding the respiratory tract, when particle sizes are sufficiently large and/or directed away from the back of the throat and deeper respiratory system.

However, use of piezo-electric materials, for instance, which produce such clouds within (or at the surfaces of) liquids, can entail several drawbacks. First, the cloud produced tends to gather aerosol particles of a very wide size distribution. The very large particles tend to entrain the smaller particles and the character of the clouds can be unsuitable for inhalation and ingestion of edible substances. Particularly, these inhaled clouds tend to have relatively small amounts of aerosolized mass, and particle sizes best suited to mouth delivery (or delivery to specific mouth surfaces) and/or to ingestion, e.g., 5-300 microns, or 60-300 microns, are not necessarily in predominant proportions. The concentration of cloud particles, over a given volume of space, may also not be suitable for delivery and/or ingestion (e.g., to provide sufficient concentration to achieve a certain dose or taste level). Also, this arrangement produces a cloud with splashing of the nature of a fountain.

Methods and apparatus to improve these conditions present challenges. For example, using a mechanical separator such as a physical screen over the aerosol generating device, with pore size greater than the desired aerosol particle size, does not necessarily allow for the easy passage of the smaller particles, and can prevent a stable standing cloud from forming.

Ingestible aerosol clouds can be produced through ultrasonication and other means which avoid these problems and present many advantages for an "inhalation" experience. Aerosol delivery devices 100 as shown in FIGS. 1A and 1B displace the aerosol cloud laterally relative to the source of the aerosol cloud such that large particles rise and fall over the source while smaller particles—particularly if lateral movement of cloud can occur very near to the surface 108 of the liquid—move by diffusion and convection laterally, escaping the falling large droplets.

The exemplary delivery device includes an aerosol delivery device that discharges an aerosolized product generally along a substantially vertical axis 118 (see e.g., FIG. 1B). Large and intermediate droplets that convect laterally fall by gravity, so if a lateral chamber exists that can contain a cloud, a cloud of fine aerosol particles exists which can be made to be a stable standing cloud. This cloud can be designed to possess particles with the desired properties by manipulation of the dimensions of the cloud container and the properties of the liquid, including surface tension of the liquid, among other manipulations. Notably, surface tensions lower than ~72 dynes/cm can be achieved with the use of surfactants that produce excellent standing cloud aerosols.

In the exemplary delivery device 100, a container attached to the aerosol delivery device defines a primary chamber 120 and a secondary chamber 122. The primary chamber 120 is hydraulically connected to the aerosol delivery device such that substantially vertical axis 118, along which the delivery device discharges particles, extends into the primary chamber 120, and particles of at least a first size tend to rise and fall along the substantially vertical axis 118. The secondary chamber 122 is adjacent and open to the primary chamber 120.

This enables the existence of two zones of the cloud, one that is substantially vertically above the ultrasound generator, and one that is displaced to the side, allowing at least a portion of the overall cloud to be relatively uniform and have the potential to be dispensed without big droplets. We have found that using mechanical separators, e.g., using a screen, between the primary chamber 120 and the secondary chamber 122, to limit spread of the larger particles, also significantly interferes with the movement of the smaller particles. The secondary chamber 122 extends horizontally outward from the primary chamber 120 such that particles smaller than the first size tend to disperse from the primary chamber 120 into the secondary chamber 122. The aerosol delivery device comprises a fluid reservoir with an ultrasonic generator. A free surface 108 of fluid in the fluid reservoir is exposed to the primary chamber 120 of the container. A lower surface of the secondary chamber 122 is angled such that liquid landing on the lower surface of the secondary chamber 122 tends to flow towards the fluid reservoir 124. Surfaces of the primary chamber include a surface extending across the substantially vertical axis 118 to limit travel of particles traveling along the substantially vertical axis 118. The surfaces of the chambers can be specifically designed and positioned to limit travel of certain particles, while also limiting splashing, and while also minimally interfering with, or encouraging, the formation of the cloud. Cloud formation is sensitive to mechanical separators and obstacles, and in some cases is substantially impeded by them, even when they are at some distance from the cloud source, and/or provide only partial interference.

The container defines an aperture extending through the container to the interior cavity. For example, the aperture 126 is vertically offset from the liquid reservoir of the aerosol delivery device when the food delivery apparatus is positioned for operation. Thus, this container defines an aperture 126 opening into the secondary chamber 122 from above.

Further, an aperture or faucet 110 can be created whereby the cloud pours into glasses or other receptacles, a convenient and useful way of consuming substances by inhalation. This aperture can be a closeable outlet 110 disposed in a lateral side surface of the container. The closeable side outlet 110 can include an aperture and a cap biased to close the aperture. In some cases, a resilient member is placed to bias the cap to cover the aperture. In some cases, the weight of the cap biases the cap to cover the aperture.

The apparatus can be a tabletop or freestanding unit including a base configured to stably support the container on a supporting surface. For example, delivery devices 100 can include/be mounted on stands as shown in FIGS. 1A and 1B. Delivery devices 100 can also be placed directly on flat surfaces such as tables.

FIGS. 2A-2D depict another aerosol dispensing device 200. Aerosol dispensing device 200 includes a body 210 with a flat bottom 211, a flat side portion 212, and an opening 213 defined generally opposite the flat bottom 211. The flat bottom 211 is sized such that it can support the aerosol dispensing device, for example, on a table or a counter as shown in FIG. 2B. The flat side portion 212 is disposed at an angle to the flat bottom 211 and is also sized such that it can support the aerosol dispensing device, for example, on a table or a counter as shown in FIG. 2C. The angle between the flat side portion 212 and the flat bottom portion 211, and the size and shape (and overall weight) of the body 210, can be designed such that placing the device 200 on the flat side portion 212 positions the opening 213 slightly above the mouth of a glass into which an aerosol cloud is being dispensed. As shown in FIG. 2C, the illustrated embodiment is configured to dispense an aerosol cloud into a 250 mL-glass.

The body 210 includes an upper portion 216 and a lower portion 218. In this embodiment, the upper portion 216 and the lower portion 218 are separate pieces that are joined together to form the body 210 (see, e.g., FIG. 2D). The lower portion 218 defines an aperture sized to receive the ultrasonic element 220. The ultrasonic element 220 provides the flat side portion 212 of the body 210.

The upper portion 216 is molded from acrylic and allows users to see the aerosol cloud within the device 200 during use. The upper portion 216 can also be formed of other materials such as, for example, clear glass, tinted glass, opaque plastics, metals, and ceramics. The lower portion 218 is machined from aluminum and can have a reflective surface on inner surfaces exposed to the inner cavity of the device 200. The lower portion 218 can also be formed of other materials such as, for example, steel and plastic.

In some embodiments, the relative orientation and position of ultrasonic element 220 and chamber surfaces (e.g., upper portion 216) can be such that the substantially vertical axis (i.e., less than 90 degrees from a perpendicular line intersecting the flat liquid surface) extending from ultrasonic element 220, intersects a surface of the chamber at a relatively short distance from the free surface of the liquid (i.e., substantially less than the distance the cloud and drops would otherwise travel), causing a significant proportion of the cloud particles and drops generated to collide rapidly with this surface. This immediately limits the extent to which the cloud and drops can splash elsewhere (including outside the chambers) and potentially interfere with the formation of the broader cloud, or cause undesirable splashing.

The ultrasonic element 220 includes piezoelectric elements 224 and a fluid sensor 226. The piezoelectric elements 224 are oriented to emit energy in a direction substantially perpendicular to the flat side portion 212. The fluid sensor 226 is connected to the piezoelectric elements 224 to trigger operation of the piezoelectric elements 224 when fluid contacts the fluid sensor 226. In operation, the device 200 can be filled with the fluid to be aerosolized to a level slightly below the fluid sensor 226 while the device 200 is positioned resting on its flat bottom 211 (see FIG. 2B). A user desiring to dispense an aerosol positions the device 200 so that it is resting on its flat side portion 212. In this position, fluid contacts the fluid sensor 226 which activates the piezoelectric elements 224.

The orientation of the piezoelectric elements 224 relative to the opening 213 provides a two-chamber effect similar to that described above with respect to delivery device 100. When the dispensing device 200 is activated, large particles or droplets rise and fall substantially vertically in line with the orientation of the piezoelectric elements 224. A cloud of smaller particles disperses laterally towards the opening 213. The energy imparted to the smaller particles by the piezoelectric elements 224, the air circulation pattern caused by the fountain of larger particles, diffusion, and other relevant forces, can allow the smaller particles to remain airborne as they move towards the opening 213. After flowing through the opening 213, the smaller particles slowly flow downwards (e.g., into the glass shown in FIG. 2C).

In this embodiment, the ultrasonic element 220 is powered by electrical current provided through electric cords 222 (see FIGS. 2B and 2C) which extend from the ultrasonic element 220 through a side port 214 (see FIGS. 2A and 2D) defined in the lower portion 218 of the body 210. In other embodiments, the ultrasonic element 220 can use other power sources including, for example, batteries.

The device 200 is filled by pouring the fluid to be aerosolized into the inner cavity through the opening 213. Some aerosol dispensing devices are refillable through ports extending through the sides of the devices.

FIGS. 3A, 3B, 4A, and 4B show aerosol dispensing devices 230 and 240, which include side ports 232 and 232', respectively. The other components of devices 230 and 240 can be substantially similar to the components of the device 200 discussed with respect to FIGS. 2A-2D.

A cartridge 234 can be used to introduce liquid into the device 230. Cartridge 234 can be configured to contain a set volume (e.g. 1 ml to 3 liters) of liquid. The cartridge 234 can be, for example, a cartridge as described in U.S. Patent App. No. 61/454,716 filed on Mar. 21, 2011 or U.S. Patent App. No. 61/528,568 filed on Aug. 29, 2011. These cartridges include a feed tube that sticks down through the center of the cartridge.

The configuration of side port 232 and cartridge 234 for device 230—in which cartridge 234 can remain substantially upright relative to gravity throughout the attachment process, and liquid in the cartridge can remain substantially below the point of attachment—can mitigate the risk of liquid in cartridge 234 spilling out while being added to device 230.

Figure 3A:
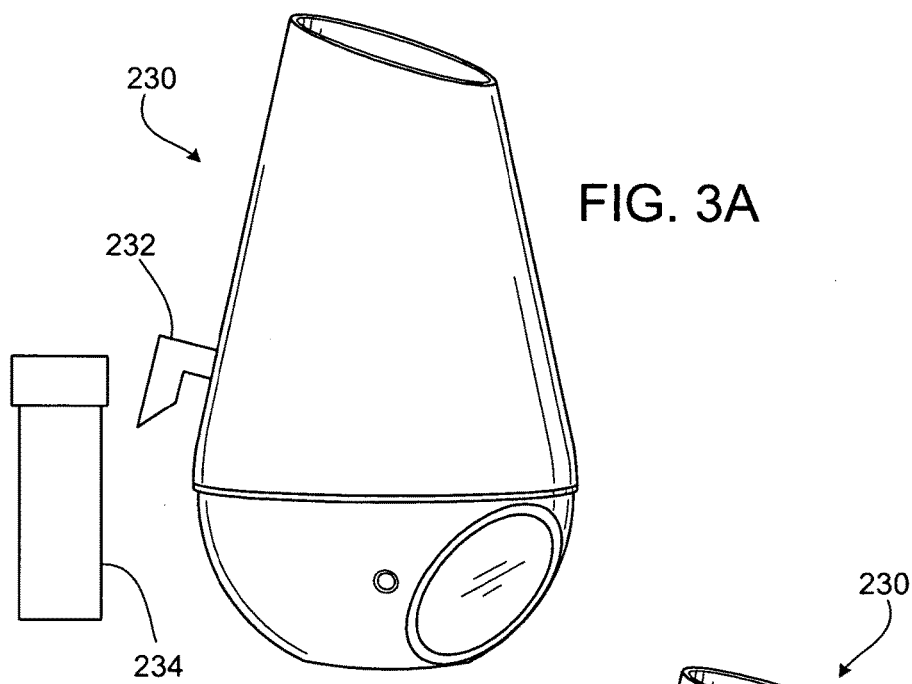
FIGS. 3A and 3B illustrate a cartridge filling system for an aerosol dispensing device.
Figure 3B:
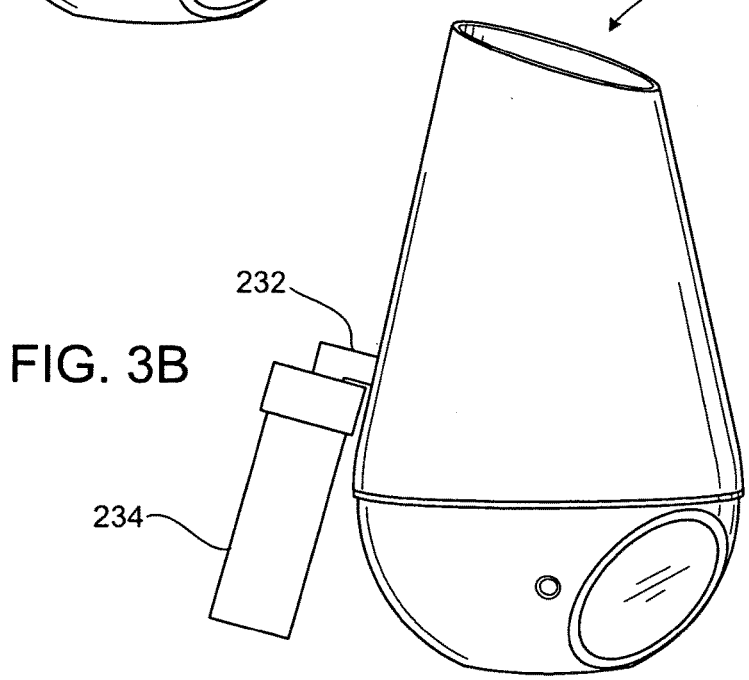
Figure 4A:
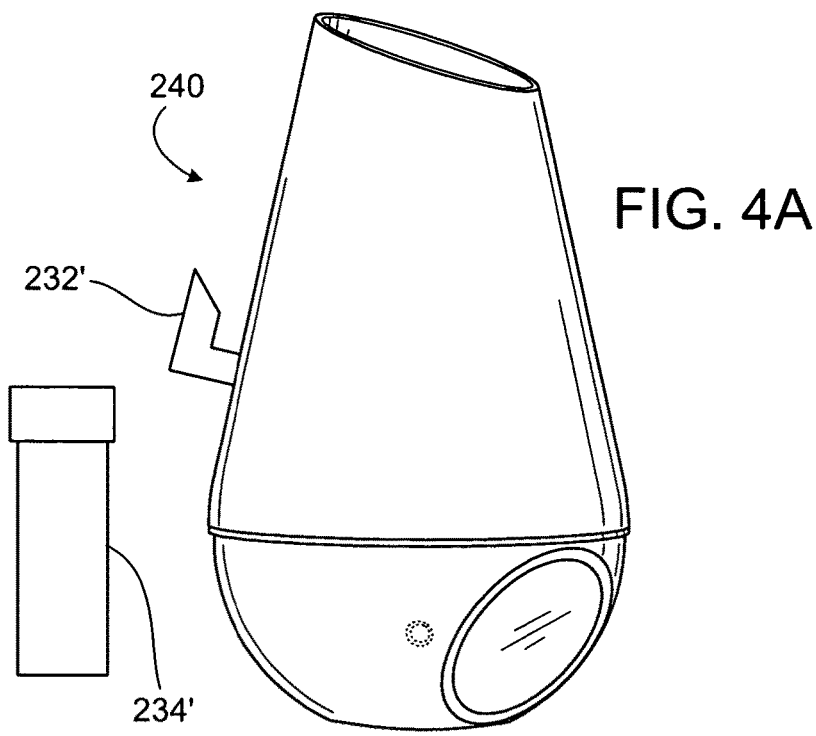
FIGS. 4A and 4B illustrate a cartridge filling system for an aerosol dispensing device.
Figure 4B:
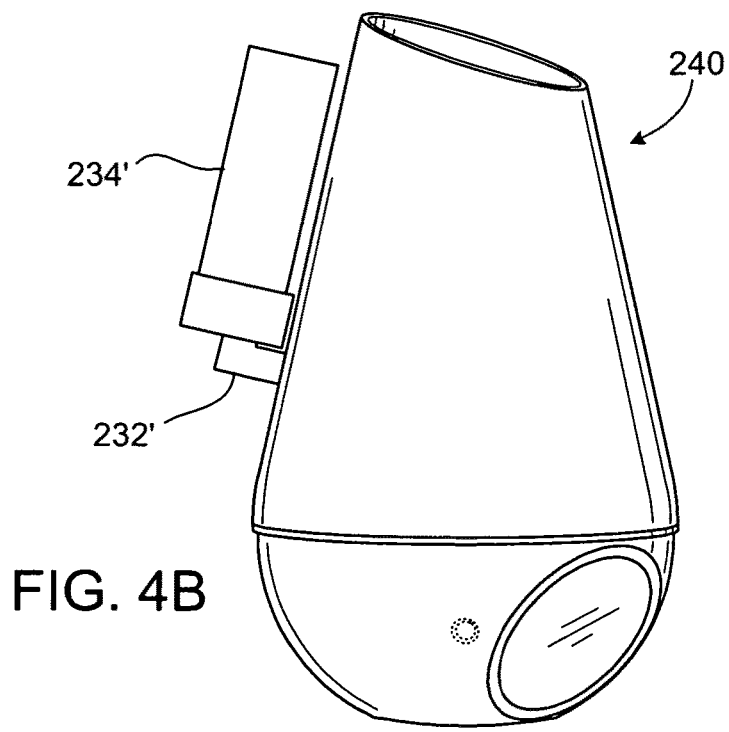

In some embodiments, a siphon effect is used to transfer liquid from the cartridge 234 to the interior of device 230. This requires the liquid in the cartridge to be in a higher position relative to gravity than the pool of liquid inside device 230. Such embodiments can include a manual lever that starts the flow of fluid from the cartridge to the device, thus starting a siphon effect, with gravity effects maintaining flow until the cartridge is empty. The exact position of side port 232 along the side of device 230 can take under consideration the need for sufficient space below side port 232 for the siphoning to be effective. For example, in order to have the liquid in cartridge 234 be completely above the pool of liquid inside device 230 when cartridge 234 is connected to side port 232, the side port 232 may be in a position higher than as shown in FIGS. 3A and 3B.

In some embodiments, connecting a cartridge 234 to the aerosol delivery device 230 activates a pump, such as an electric pump, that creates a suction that pulls liquid out of the cartridge 234 and into aerosol delivery device 230. In some embodiments, the pump is activated by activation of the piezoelectric elements 224. In some embodiments, the pump is activated using a manual on/off switch.

In some embodiments, as illustrated with device 240, liquid can be prevented from spilling out of cartridge 234' even if the liquid in the cartridge is substantially above the connection point between the cartridge 234' and the side port 232'. In some embodiments, a valve mechanism may be used so that gravity causes fluid in the cartridge 234' to flow into the aerosol dispensing device 240. In some embodiments, a siphon effect may be used.

The cartridge-filling approaches at least partially address the issue that exists for the delivery of nutrients given the low concentration of nutrients in the aerosol and the sparseness of the aerosol. For example, the mass of nutrient per aspiration is extremely small in these liquid-based aerosol clouds relative to a dry powder aerosol. One way around this is to concentrate a liquid, e.g. increase dramatically the concentration of caffeine, or vitamin C, etc. However, this concentration can lead to dangerous reactions if such a liquid would be consumed as a drink. Associating the means of releasing such liquid from the storage cartridge with actually dispensing the liquid into the aerosol dispenser reduces the likelihood that the liquid will be drunk rather than an aerosol breathed by the user.

More generally, a cartridge for use in association with an aerosol dispensing device may contain substances not in a form appropriate for consumption, but by virtue of the association with the dispensing device, become appropriate for consumption. "Appropriate for consumption" may, for example, refer to such qualities as being in an amount or concentration that is non-toxic, healthy, or imparts a preferred taste; or that it no longer has an undesirable constituent. In some embodiments, the generation of the cloud may lead to physical or chemical effects—such as heating, or separation of solid or liquid components (e.g. certain solid particles may stay in the liquid and not rise into the cloud)—which may alter the properties or proportions of components in the cloud, relative to their properties or proportions in the cartridge. This may be used to enable or enhance consumption.

As noted, in some embodiments, the contents of the cartridge is not necessarily the same, or its components are not found in the same proportions, as the contents to be dispensed by the aerosol dispensing device. Such cartridges may, for example, contain a mixture of solids and liquids, and upon association with the aerosol dispensing device, a filter or other mechanism may favor the entry of one substance (e.g., the liquid) over another (e.g., the solid) into the dispenser. In some embodiments, a cartridge may contain a concentrated substance that is diluted by separate addition of a diluent (e.g., water). Combinations of cartridges associated with a single aerosol dispensing device are also possible. The aerosol dispensing devices described above, as well as other aerosol dispensing devices such as are described in WO 2010/065744 filed on Dec. 3, 2009, the entire contents of which are incorporated herein by reference, can be used to dispense an aerosol cloud into a glass.

Figure 5A:
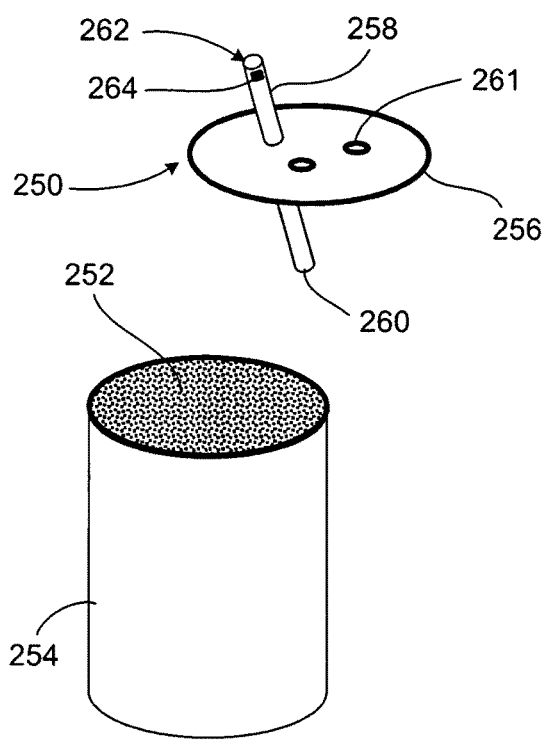
FIGS. 5A and 5B illustrate a cover configured to keep an aerosol cloud in a glass.
Figure 5B:
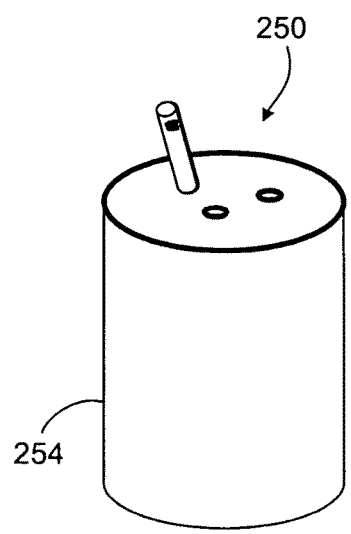
Figure 6:
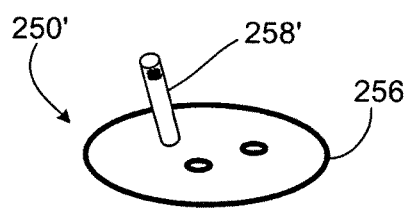
FIG. 6 illustrates a cover configured to keep an aerosol cloud in a glass.
Figure 7:
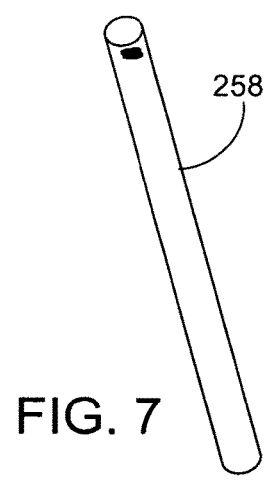
FIGS. 7 and 8 illustrate straws configured for sipping an aerosol cloud.
Figure 8:
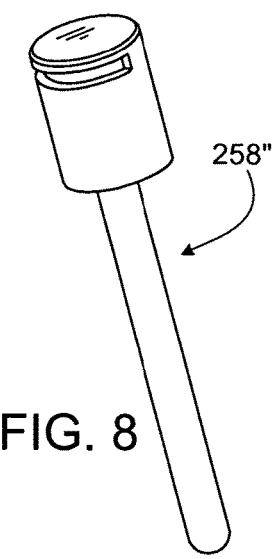
Figure 9A:
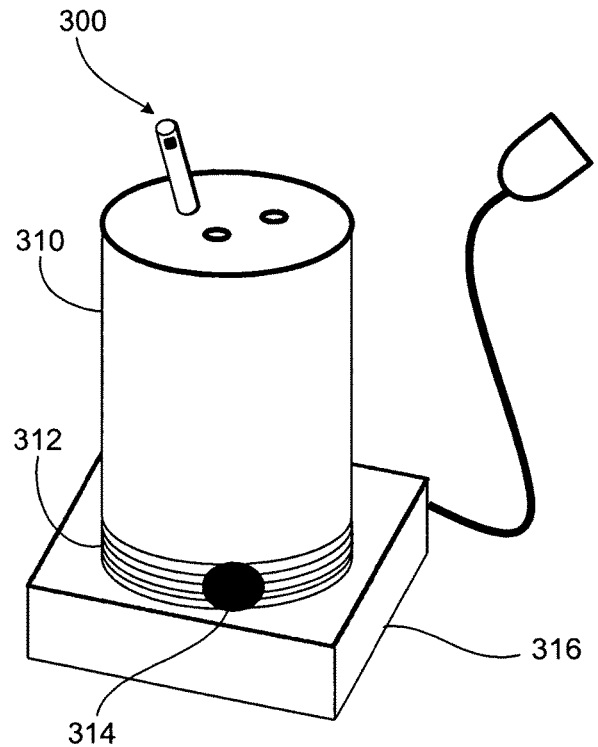
FIGS. 9A and 9B illustrate a "single serving" aerosol dispenser.
Figure 9B:
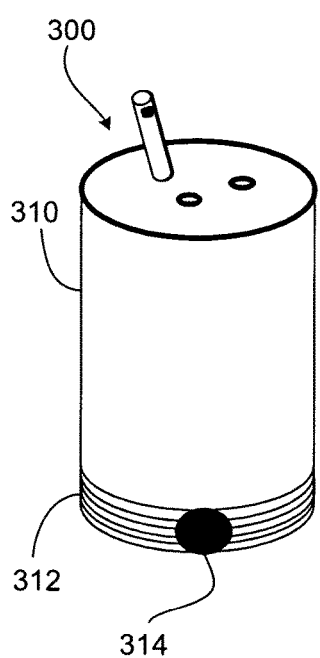
Figure 9B:
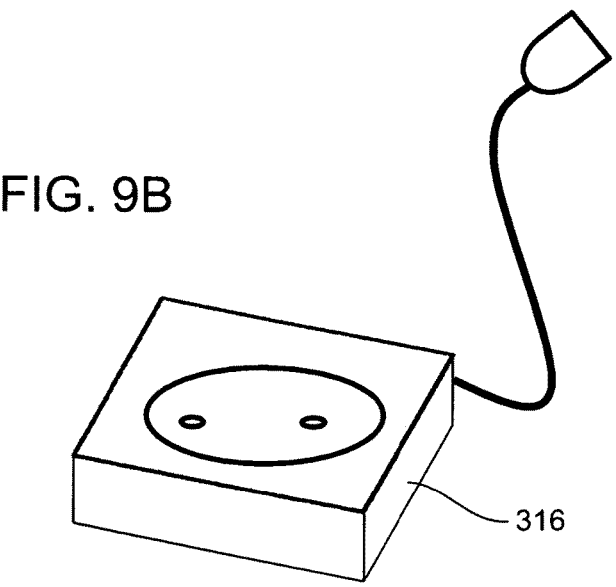
Figure 10A:
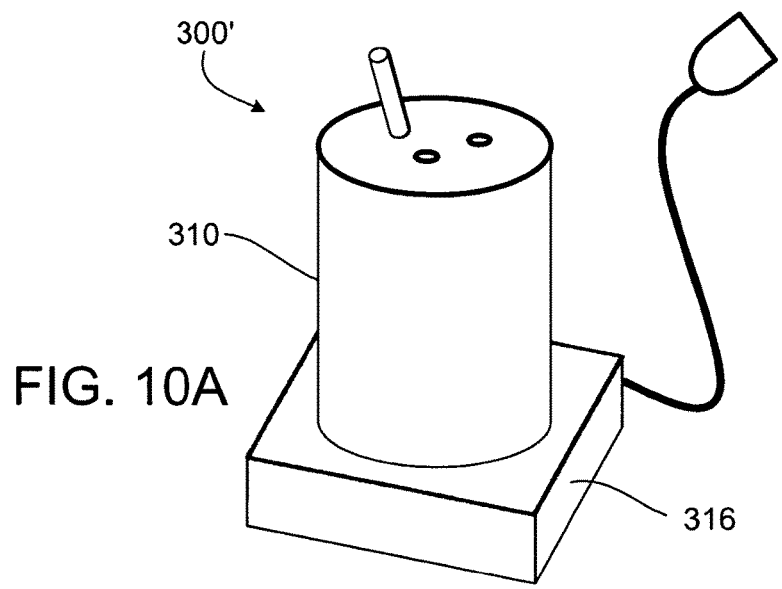
FIGS. 10 A and 10B illustrate a "single serving" aerosol dispenser.
Figure 10B:
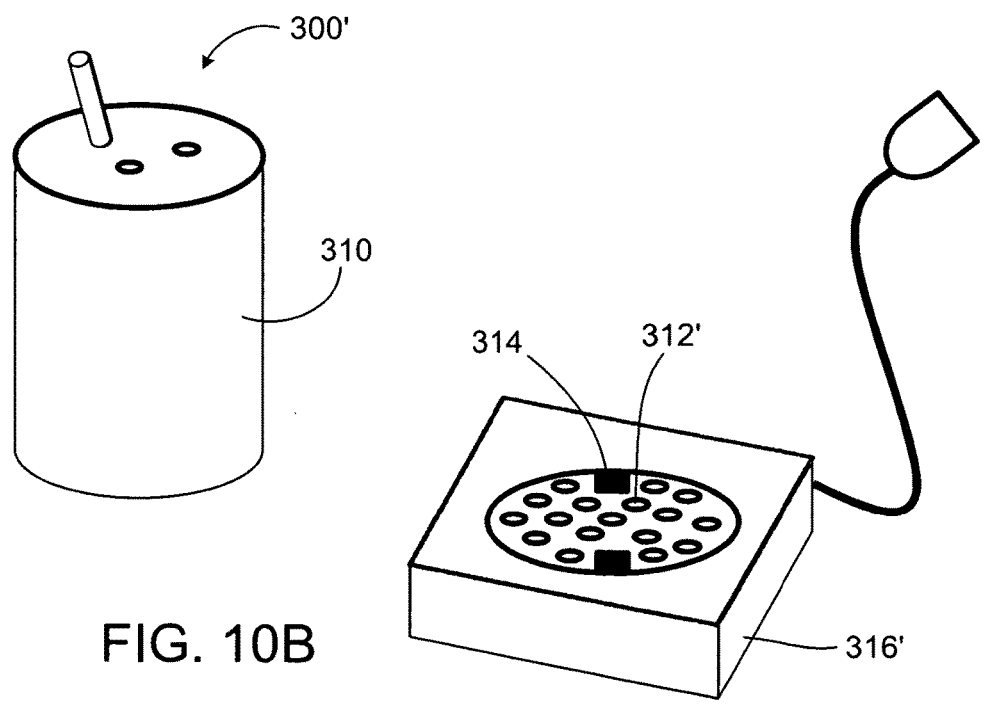

FIGS. 5A and 5B illustrate a cover 250 configured to be used to keep an aerosol cloud 252 in a glass, for example, as a user walks away from device 200 after dispensing an aerosol cloud 252 into the glass 254. It is intended to address the general problem of convection causing the aerosol cloud to disperse, settle, or otherwise be difficult to consume, when it is transported. The cover 250 includes a primary member 256 with a straw 258 that extends through the primary member 256. In this embodiment, both the primary member 256 and the attached straw 258 are formed of glass. In this embodiment the primary member 256 is designed to have an opening through which a separate straw 258 can be inserted. In some embodiments, the primary member 256 and straw 258 are permanently attached to each other as a single unit. In general, the primary member 256 is designed to have a size and shape appropriate for substantially covering the glass 254 intended to be used in conjunction with it and with the aerosol dispensing device. In other embodiments, the glasses used with the aerosol dispensing device have diameters of approximately 5-8 centimeters, and thus the primary member 256 has a comparable diameter. The primary member 256 can, for example, be a larger disc that extends beyond the diameter of the glass 254, and has a greater diameter. It can also be specifically designed to fit closely atop a specific glass. In some embodiments, the thickness of a glass primary member 256 can vary from approximately 1 millimeter to 1 centimeter, or in some cases much more, for example if it incorporates a hollow interior or a decorative feature.

In this embodiment, the primary member is a substantially disc-shaped member. The underside of the primary member 256 is generally flat. This configuration facilitates use of the cover 250 with any glass whose diameter is smaller than the diameter of the cover 250, and whose top surfaces are flat enough so that the primary member 256 is able to sufficiently cover the opening of the glass. In some embodiments, the underside of the primary member 256 includes flanges extending downward from the primary member 256 to fit around the outside, extend into the inside, or both, of glasses 254 with a specific diameter. In some cases, the covers 250 and associated glasses 254 are manufactured as a matched set with the covers sized such that the flanges engage the glasses 254 to hold to hold the covers 250 in position.

The upper side of the illustrated primary member 256 is also substantially flat. In some embodiments, the primary member 256 has other shapes. For example, some primary members 256 are dome-shaped and some primary members 256 are spherical. In some embodiments, the underside of the primary member 256 is convex when viewed from below, such that the middle area of primary member 256 extends further toward the bottom of glass 254, than the "rim" region of primary member 256 located further away from the center of primary member 256. This can also facilitate the use of cover 250 with a variety of glasses, by helping to prevent the cover 250 from sliding off the glass.

The straw 258 is generally tubular extending from an open inlet end 260 through the primary member 256, to a mouthpiece 262 with side outlets 264. When a user inhales through the straw 258, the configuration of the mouthpiece directs aerosol drawn through the straw sideways (e.g., towards the tongue and taste buds). We have found that a straw with a mouthpiece with side outlets provides a stronger taste experience than a conventional straw, and reduces the likelihood of particles extending toward the back of the throat and further into the respiratory tract. We hypothesize that the improved results are due to changes in where the aerosol strikes mouth surfaces, and concentrating effects of the mouthpiece such as the mouthpieces and deflection members described in WO 2010/065744 filed on Dec. 3, 2009, the entire contents of which are incorporated herein by reference.

Such mouthpiece effects can also play a role in the delivery of nutrients, vitamins, dietary supplements, or other particles in which the aerosol concentration is important. For example, the straw mouthpiece may enable the concentration of a nutrient to reach a level that is appropriate to have a positive impact on the health or wellness of the user.

In some embodiments, the cover 250 is made of rigid materials, such as ceramics or metals. In some embodiments, the cover 250 is made of less rigid materials, such as fabric, paper, plastic, film materials, etc.

In some embodiments, a gasket material (not shown) extends in an annulus around the perimeter of the underside of the primary member 256. The gasket material provides both a cushioning buffer and a seal between the glass 254 and the cover 250. A gasket material can also be used between a primary member 256 and a straw 258, or other components of a cover system 250.

The primary member 256 defines passages that allow ambient air to enter the glass 254 when a user inhales through the straw 258. In this embodiment, holes 261 extend through the primary member 256 to provide these air passages. In some embodiments, these passages are provided not by well-defined holes but by less conspicuous spaces between the glass 254 and the primary member 256. For example, in many cases, a primary member 256 made of glass or other relatively rigid material, when placed atop a rigid glass 254, will not create a seal that substantially impedes airflow between the external environment, and the interior of glass 254. In some embodiments, primary member 256 provides airflow between the external environment and the interior of glass 254 by being "folded over" to a certain extent, for example if the material is paper, flexible plastic, or fabric. In some embodiments, the airflow is provided by the porosity of primary member 256, for example, if it is a fabric through which air can travel enough to provide airflow inside the glass 254 upon inhalation, but not so much as to allow convective currents to substantially disrupt the cloud.

The general concepts implemented in the cover 250 illustrated in FIGS. 5A and 5B can be expressed in other devices. For example, FIG. 6 illustrates another cover 250' in which the straw 258' only extends upwards from the primary member 256 rather than through the primary member 256. The cover 250' can be used with glasses of different heights. However, the cover 250, in which the straw extends to a considerable extent toward the bottom of glass 254, is anticipated to be more effective at continuing to provide a favorable taste experience as the aerosol cloud is consumed and/or settles in the glass. In another example, FIG. 7 illustrates a straw 258 that is not attached to a cover 250. Such standalone straws can be used, for example, with a cover 250 in which a straw device is not affixed to the primary member 256, or to sip aerosol directly from a dispenser such as dispenser 100 without first transferring the aerosol cloud to a glass. FIG. 8 illustrates a similar standalone straw 258" which incorporates a mouthpiece which some users find more confortable to use. In some embodiments, the straw can be made by connecting a mouthpiece element with the desired airflow-directing properties, to a generally cylindrical element that provides sufficient length for convenient use with a cover device or aerosol dispenser.

The aerosol dispensers 100, 200 discussed above with respect to FIGS. 1A-4B can be used to prepare and dispense multiple servings of aerosolized substances to a group of users. "Single serving" aerosol dispensers can also implemented, in a manner similar to having single glasses of a liquid beverage FIGS. 9A and 9B illustrate a single serving aerosol dispenser 300. The illustrated single aerosol dispenser 300 is a glass 310 that incorporates piezoelectric elements 312 in its base. A switch 314 on the glass 310 activates and deactivates the piezoelectric elements 312. The piezoelectric elements 312 are powered by rechargeable batteries contained within the dispenser 300. The single serving aerosol dispenser 300 can be stored on a charger 316. A cover and/or straw as described above with respect to FIGS. 5A-8 is optionally provided with the single serving aerosol dispenser 300.

A user can fill the single serving aerosol dispenser 300 with, for example, orange juice or martini. The user carries the glass 310 and, when desired, operates the switch 314 to generate an aerosol cloud. The illustrated single serving aerosol dispenser 300 does not have the two-zone structure for the cloud described above with respect to the aerosol dispensers 100, 200 and with respect to FIGS. 1A-4B, in which the cloud to be consumed may extend away from the surface of the pool of liquid. In this embodiment of dispenser 300, the aerosol cloud forms just above the liquid. However, the user can operate the piezoelectric elements 314 for just a few seconds (enough to make the cloud) and can then shut them off. The cloud remains, so the user has the tranquil cloud to sip from and can either drink the liquid or sip the aerosol cloud. In some embodiments, the glass 310 is configured to provide the two-zone structure described above with respect to the aerosol dispensers 100, 200 discussed above with respect to FIGS. 1A-4B.

FIGS. 10A and 10B illustrate another single serving aerosol dispenser 300'. In this version, the piezoelectric elements 312' are part of the base 316' rather than incorporated into the glass 310. The piezoelectric elements 312' can be activated when the glass 310 is placed on the base 316' such that the glass 310 engages the contacts 314' on the base 316'. In this embodiment, when the glass 310 is on the base 316', liquid would be in communication with the piezoelectric elements 312', in such a way as to allow for the generation of an aerosol cloud above the liquid. For example, the liquid can be in direct hydraulic contact with the piezoelectric elements, or it can be separated by some kind of barrier, such as a thin, substantially non-porous film, that can hold the liquid in the glass above but not impede the transfer of energy from the piezoelectric elements into the liquid, which is necessary to generate the cloud.

Once the cloud has formed and the user wishes to take the glass off the base, the piezoelectric elements would be turned off (automatically or manually) and the liquid would be separated from the piezoelectric elements and base. In some embodiments, this involves the introduction of a seal between the glass and the base, to hold the liquid in the glass above and prevent it from spilling upon detachment from the base. In some embodiments in which some kind of barrier already exists between the liquid and the base, it may be necessary to reinforce this barrier for physical strength, for example, by adding a rigid layer to a relatively weak film barrier already present.

In order to assess the effectiveness of a cover system 250, a primary member 256 made of paper film was placed atop a variety of glasses 254, and the time for the cloud to substantially settle (without the introduction of a straw and without any consumption by a user) was measured. The results include: Champagne Flute (200 mL volume; 5.1 cm diameter)—Lifetime of cloud with cover: 1 min 59 s; Large tall glass (250 mL volume; 5.8 cm diameter)—Lifetime of cloud with cover: 2 min 09 s; "Whaf glass" (250 mL volume; 5.5 cm diameter)—Lifetime of cloud with cover: 1 min 53 s; Whiskey glass (260 mL volume; 7.4 cm diameter)—Lifetime of cloud with cover: 1 min 15 s; and Wine glass (300 mL volume, 7 cm diameter)—Lifetime of cloud with cover: 2 min 41 s.

It is hypothesized that the cover system is able to extend the lifetime of an aerosol cloud within a glass 254 by, at least in part, preventing to some extent convection from: blowing the cloud away from glass 254; and/or causing the cloud to collide with the sides of glass 254; and/or causing the cloud particles to collide with each other; all of which may help accelerate the settling or dispersal of the cloud.

It is hypothesized that the volume in which the cloud exists within glass 254 and under cover system 250, and the surface area of the boundaries of this volume, play a role in the lifetime of the cloud. For example, if the surface-area-to-volume ratio is high, the cloud particles generally have a higher probability of colliding into one of the boundaries, and the cloud lifetime would be expected to be reduced. The preliminary findings noted here suggest this trend may indeed exist.

A number of embodiments have been described. Nevertheless, it will be understood that various modifications may be made without departing from the spirit and scope of the disclosure. Accordingly, other embodiments are within the scope of the following claims.

What is claimed is:

1. A device for generating an aerosol cloud, the device comprising:
    a body defining an inner cavity, an outer surface, and an opening extending between the inner cavity of the body and the outer surface, and the body having a flat bottom portion and a flat side portion;
    at least one ultrasonic element operable to aerosolize a liquid disposed in the inner cavity; and
    at least one sensor associated with the at least one ultrasonic element,
    wherein the body has a first stable equilibrium position in which the device rests on the flat bottom portion and a second equilibrium position in which the device rests on the flat side portion such that the opening is higher when the body is in the first stable equilibrium position than when the body is in the second equilibrium position and such that the at least one ultrasonic element is operable to emit energy substantially vertically when the body is in the second equilibrium position.

2. The device of claim 1, wherein the at least one ultrasonic element comprises a piezoelectric element.

3. The device of claim 1, wherein the at least one sensor is a fluid sensor.

4. The device of claim 1, wherein the at least one ultrasonic element is disposed within the body defining the inner cavity.

5. The device of claim 1, wherein the at least one ultrasonic element is operable to emit energy substantially along an axis that is offset from the opening extending between the inner cavity of the body and the outer surface of the body.

6. The device of claim 1, wherein the sensor activity is determined by an orientation of the body.

7. The device of claim 1, wherein the at least one sensor activates the at least one ultrasonic element in the presence of liquid or deactivates the at least one ultrasonic element in the absence of liquid.

8. The device of claim 1, further comprising a port configured to engage a fluid cartridge.

9. A system comprising:
    a container having a flat bottom portion and a flat side portion, and defining an inner cavity having a volume of between about 6 ounces and 20 ounces with an opening; and
    at least one ultrasonic element operable to aerosolize a liquid disposed in the inner cavity defined by the container,
    wherein the container has a first stable equilibrium position in which the container rests on the flat bottom portion and a second equilibrium position in which the container rests on the flat side portion such that the opening is higher when the container is in the first stable equilibrium position than when the container is in the second equilibrium position and such that the at least one ultrasonic element is operable to emit energy substantially vertically when the container is in the second equilibrium position.

10. The system of claim 9, wherein the at least one ultrasonic element is operable to emit energy substantially along an axis that is offset from the opening.

11. The system of claim 9, further comprising a port configured to engage a fluid cartridge.

* * * * *